United States Patent
Regere et al.

(10) Patent No.: US 9,757,101 B2
(45) Date of Patent: Sep. 12, 2017

(54) DEVICE FOR CONTROLLING A SURGICAL HANDPIECE

(71) Applicant: SOCIETE POUR LA CONCEPTION DES APPLICATIONS DES TECHNIQUES ELECTRONIQUES, Merignac (FR)

(72) Inventors: Pascal Regere, Blanquefort (FR); Charles Reche, Bordeaux (FR); Yann Gallard, Le Haillan (FR)

(73) Assignee: SOCIETE POUR LA CONCEPTION DES APPLICATIONS DES TECHNIQUES ELECTRONIQUES, Merignac (FR)

( * ) Notice: Subject to any disclaimer, the term of this patent is extended or adjusted under 35 U.S.C. 154(b) by 207 days.

(21) Appl. No.: 14/436,936

(22) PCT Filed: Oct. 3, 2013

(86) PCT No.: PCT/FR2013/052355
§ 371 (c)(1),
(2) Date: Apr. 20, 2015

(87) PCT Pub. No.: WO2014/060676
PCT Pub. Date: Apr. 24, 2014

(65) Prior Publication Data
US 2015/0265259 A1    Sep. 24, 2015

(30) Foreign Application Priority Data
Oct. 18, 2012 (FR) .................................. 12 59927

(51) Int. Cl.
*A61B 17/00* (2006.01)
*A61C 1/00* (2006.01)
(Continued)

(52) U.S. Cl.
CPC ............ *A61B 17/00* (2013.01); *A61C 1/0015* (2013.01); *A61C 1/07* (2013.01); *A61C 17/0202* (2013.01);
(Continued)

(58) Field of Classification Search
CPC ................ A61B 17/00; A61B 17/1626; A61B 2017/00212; A61B 2017/00221;
(Continued)

(56) References Cited

U.S. PATENT DOCUMENTS 4,633,514 A * 12/1986 Fimoff ..................... H04N 5/44
                                                    341/22
5,368,015 A * 11/1994 Wilk .................. A61B 1/00147
                                                    128/903
(Continued)

FOREIGN PATENT DOCUMENTS

WO      2011141442 A1    11/2011

OTHER PUBLICATIONS

International Search Report for corresponding International PCT Application No. PCT/FR2013/052355, Dec. 20, 2013.

*Primary Examiner* — An T Nguyen
(74) *Attorney, Agent, or Firm* — Workman Nydegger (57) ABSTRACT

A control device for controlling a surgical handpiece is suitable for controlling the surgical handpiece according to control parameters. The control device comprises local control means present on the control device, wireless communication means suitable for communicating with remote control means by a wireless communication link. The local control means and the wireless communication means is suitable for receiving instructions to adjust each control parameter. Selector means is provided for selecting either the local control means or the wireless communication means for adjusting each control parameter.

16 Claims, 5 Drawing Sheets

(51) Int. Cl.
    *A61C 1/07*     (2006.01)
    *A61C 17/02*     (2006.01)
    *G05B 15/02*     (2006.01)
    *A61C 17/20*     (2006.01)
    *A61B 17/16*     (2006.01)

(52) U.S. Cl.
    CPC .......... *G05B 15/02* (2013.01); *A61B 17/1626* (2013.01); *A61B 2017/00212* (2013.01); *A61B 2017/00221* (2013.01); *A61B 2217/007* (2013.01); *A61B 2560/0204* (2013.01); *A61C 17/20* (2013.01)

(58) Field of Classification Search
    CPC ...... A61B 2560/0204; A61B 2217/007; G05B 15/02; A61C 1/07; A61C 17/20; A61C 17/0202; A61C 1/0015; A61C 1/0023; G08C 19/00
    See application file for complete search history.

(56) References Cited

U.S. PATENT DOCUMENTS

| | | | | |
|---|---|---|---|---|
| 5,874,789 A * | 2/1999 | Su | ........................ | C07C 68/005 307/140 |
| 7,430,453 B2 * | 9/2008 | Scalf | .................. | G05B 19/0426 700/19 |
| 8,638,191 B2 * | 1/2014 | Hamel | ................... | A61B 17/00 340/10.1 |
| 9,607,508 B2 * | 3/2017 | Lint | ..................... | A61C 1/0015 |
| 2005/0251228 A1 * | 11/2005 | Hamel | ............. | A61B 17/32002 607/60 |
| 2006/0116667 A1 * | 6/2006 | Hamel | ............. | A61B 17/32006 606/1 |
| 2007/0254261 A1 * | 11/2007 | Rosenblood | ......... | A61C 1/0015 433/98 |
| 2009/0085718 A1 * | 4/2009 | Hamel | ................... | A61B 17/00 340/5.5 |
| 2009/0121865 A1 * | 5/2009 | Hamel | ............... | A61B 1/00006 340/539.17 |
| 2010/0077109 A1 * | 3/2010 | Yan | ..................... | H04L 43/0811 710/17 |
| 2012/0064483 A1 * | 3/2012 | Lint | ..................... | A61C 1/0023 433/101 |
| 2013/0116805 A1 * | 5/2013 | Frochaux | ............. | A61C 1/0015 700/83 |
| 2013/0162515 A1 * | 6/2013 | Prociw | .................. | G06F 1/1616 345/156 |
| 2014/0017629 A1 * | 1/2014 | Lint | ..................... | A61C 1/0023 433/101 |
| 2014/0266636 A1 * | 9/2014 | Larsen | ................... | G08C 19/16 340/12.5 |
| 2014/0344494 A1 * | 11/2014 | Zeung | .................. | G06F 1/1632 710/303 |
| 2015/0265259 A1 * | 9/2015 | Regere | ................ | A61C 1/0015 700/275 |

* cited by examiner

DEVICE FOR CONTROLLING A SURGICAL HANDPIECE

BACKGROUND OF THE INVENTION

The present invention relates to the field of surgical handpieces such as those used for dental or medical care, and it relates more particularly to an appliance for controlling such a handpiece.

The present invention relates in particular to scalers, to micromotors, and to prophylactic, diagnostic, imaging, or surgical appliances.

The space occupied in dental or medical surgeries by the equipment used by the practitioner is a recurrent problem that is due both to the numerous wired links comprising supply cords for delivering electricity or fluids to surgical handpieces, and also to the multiple links with the associated control systems.

Figure 1:
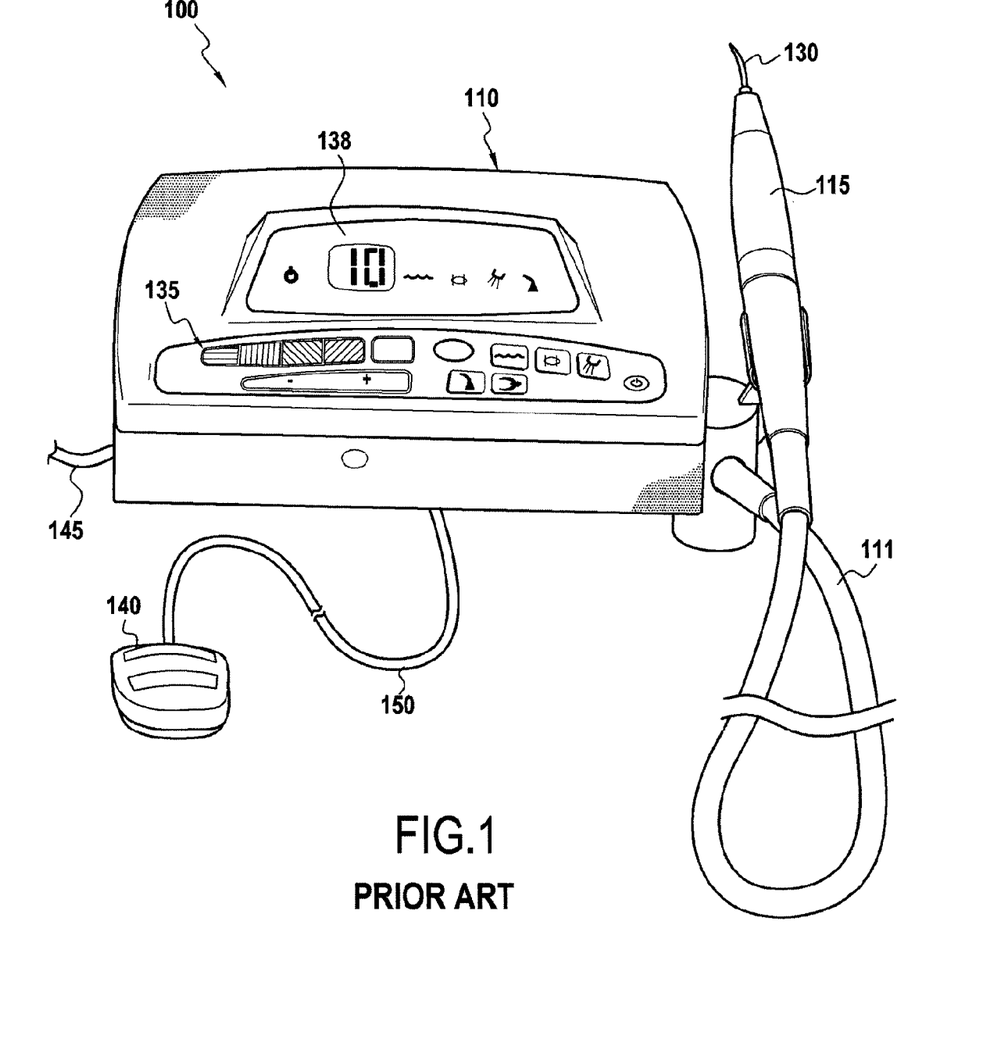
FIG. 1, described above, is a diagrammatic view of an example of a dental care appliance having a surgical handpiece.

This applies for example in dentistry for appliances for removing scale. As shown in FIG. 1, a scaler appliance 100 typically comprises a control device 110 (i.e. a central unit) that serves in particular to generate ultrasound, the device being connected to the surgical handpiece 115 by a cord 111. A sonotrode or ultrasound insert 130 is mounted on the top or distal portion of the handpiece 115. In well-known manner, the handpiece 115 has a piezoelectric transducer (not shown) that is mechanically coupled to the insert 130 so as to transmit ultrasound vibration thereto at amplitudes that are a function of the electrical power delivered by the ultrasound generator.

The control device 110 may also feed the handpiece 115 with irrigation fluid via the cord 111 and with the help of an irrigation pump (not shown).

The front face of the control device 110 in this example includes a man-machine interface constituted by keys 135 and a screen 138. This interface enables the operator to adjust control settings such as the electrical power delivered to the handpiece 115 and the irrigation rate generated by the irrigation pump.

The system is also frequently fitted with a wired control pedal 140 enabling the operator to adjust the control parameters by foot.

Such a scaler appliance thus has three types of connection, namely: a first connection for powering the control device 110; a second connection (i.e. the cord 111) for connecting the handpiece 115 to the control device 110; and a third connection 150 for connecting the control device 110 to the pedal 140.

The increasing number of pieces of equipment present in dental or medical surgeries makes it necessary to rationalize the ways they are connected together and to reduce the space they occupy.

Various solutions have been provided, in particular by using control devices that are capable of communicating over a wireless link of the unidirectional or bidirectional type with a remote control. This type of wireless link may operate in application of various standards, such as a Bluetooth™ (registered trademark) protocol, for example (in compliance with IEEE Standard 802.15.1).

Nevertheless, other protocols can be used such as the following protocols: WiFi, Zigbee, and NFC, which correspond respectively to the following standards: IEEE 802.11, IEEE 802.15.4, and ISO/CEI 1444.

Remote control makes it advantageously possible to eliminate certain wired links such as those connecting the control pedal to the central unit, for example. One particular configuration is described for example in document US 2012/0064483 A1.

Nevertheless, wireless control devices for a surgical handpiece present certain risks in terms of safety associated with the particular uses to which these appliances are put.

It can happen that the control device suffers a malfunction and that its wireless communication link becomes degraded, interrupted, or cannot be properly established with the remote control. Such a failure may result from various problems such as a software bug, a flat battery, operator error, . . . It can also happen that the wireless link is disturbed by the outside environment (interference from nearby wireless devices, for example).

It can also happen that there is conflict between two control systems used in parallel, a wired system and a wireless system.

Other emergency situations can also occur if the remote control is not within the operator's reach (or if the remote control is actuated in error by a third party) and the operator seeks to regain control over the handpiece quickly.

Medical interventions performed using such surgical handpieces are generally difficult so it is essential for the operator to have full control over the control settings of the appliance.

There therefore exists a need for a control device that mitigates the drawbacks of present devices, and in particular for a control device that makes it easier to adjust control settings, while providing safer control of the handpiece.

OBJECT AND SUMMARY OF THE INVENTION

To this end, the present invention provides a control device for controlling a surgical handpiece, the device being suitable for controlling the surgical handpiece according to at least one control parameter, the control device comprising:

local control means present on the control device;

wireless communication means suitable for communicating with remote control means by a wireless communication link, the local control means and the wireless communication means being suitable for receiving instructions to adjust each control parameter; and selector means for selecting either the local control means or the wireless communication means for adjusting each control parameter.

The invention makes it possible advantageously to make secure the adjustment of control parameters (or control settings) of the surgical handpiece. By means of the invention, it is in particular always possible for the operator to regain control of the handpiece quickly in the event of a failure occurring in the wireless communication or in the event of any emergency situation (as explained above, there can be multiple types of emergency situation).

The control device of the invention advantageously makes it possible to define priority levels between the local control means and the remote control means: for example in the event of a failure in receiving or processing adjustment instructions issued by the remote control means, it is still possible for the operator to regain control of the handpiece.

The selector means serve in particular to define which of the means among the local control means and the wireless communication means are to be taken into account by the control device of the invention for the purpose of adjusting control settings of the handpiece. In particular when the local control means are selected, instructions that might be received via the wireless communication means of the invention are ignored, thus making it possible to avoid any erroneous setting of the handpiece. Control over the handpiece is thus made more secure.

In a first embodiment, the local control means include a removable portion;

the control device also comprising detector means for detecting the presence of the removable portion on the control device;

the selector means being configured to select the local control means automatically for adjusting each control parameter in the event of the presence of said removable portion being detected.

In this first embodiment, as soon as the removable portion is in its working position, the local control means have priority over the remote control means, i.e. the local control means are selected by the selector means. Consequently, instructions issued by the terminal are ignored, and only instructions coming from the local control means are taken into account for adjusting the handpiece.

In a second embodiment, the selector means comprise a manually-operable switch for selecting either the local control means or the wireless communication means for adjusting each control parameter.

In this second embodiment, the operator can at any time use the switch to select either the local control means or the remote communication means. Thus, in the event of a failure of the wireless communication link (or in any other emergency situation), the operator can quickly regain control over the surgical handpiece by selecting the local control means for adjusting the control settings. In this way, the control device is forced to ignore all instructions that might come from the remote control means via the wireless communication link.

Furthermore, the wireless communication link may be of the Bluetooth™ type, or may be a link complying with any of the other protocols mentioned above (WiFi, Zigbee, and NFC).

Furthermore, the local control means may comprise a Hall effect magnetic button.

In a particular embodiment, the handpiece includes a piezoelectric transducer, said at least one parameter comprising at least one of the following: an electrical power level to be delivered to the handpiece; an irrigation flow rate for the handpiece; and activating or deactivating the handpiece.

Correspondingly, the invention also provides an apparatus for controlling a surgical handpiece, the apparatus comprising:

a control device as defined above;

a handpiece having control parameters that are adjusted by said control device; and remote control means suitable for communicating with the wireless communication means of the control device via a wireless link.

The remote control means may be a communications module of the digital tablet type, of the mobile telephone type, or any other equivalent device.

BRIEF DESCRIPTION OF THE DRAWINGS

Other characteristics and advantages of the present invention appear from the following description made with reference to the accompanying drawings that show an embodiment having no limiting character. In the figures.

DETAILED DESCRIPTION OF VARIOUS EMBODIMENTS

As mentioned above, the invention relates to the field of surgical handpieces such as those used for dental or medical care, and the invention relates more particularly to a control device for such a handpiece.

Below in this document, the embodiments of the invention that are described relate to the specific situation of a control device for a surgical handpiece that is suitable for removing dental scale. Nevertheless, it will be understood that the invention applies more generally to any control device for a surgical handpiece.

Figure 2:
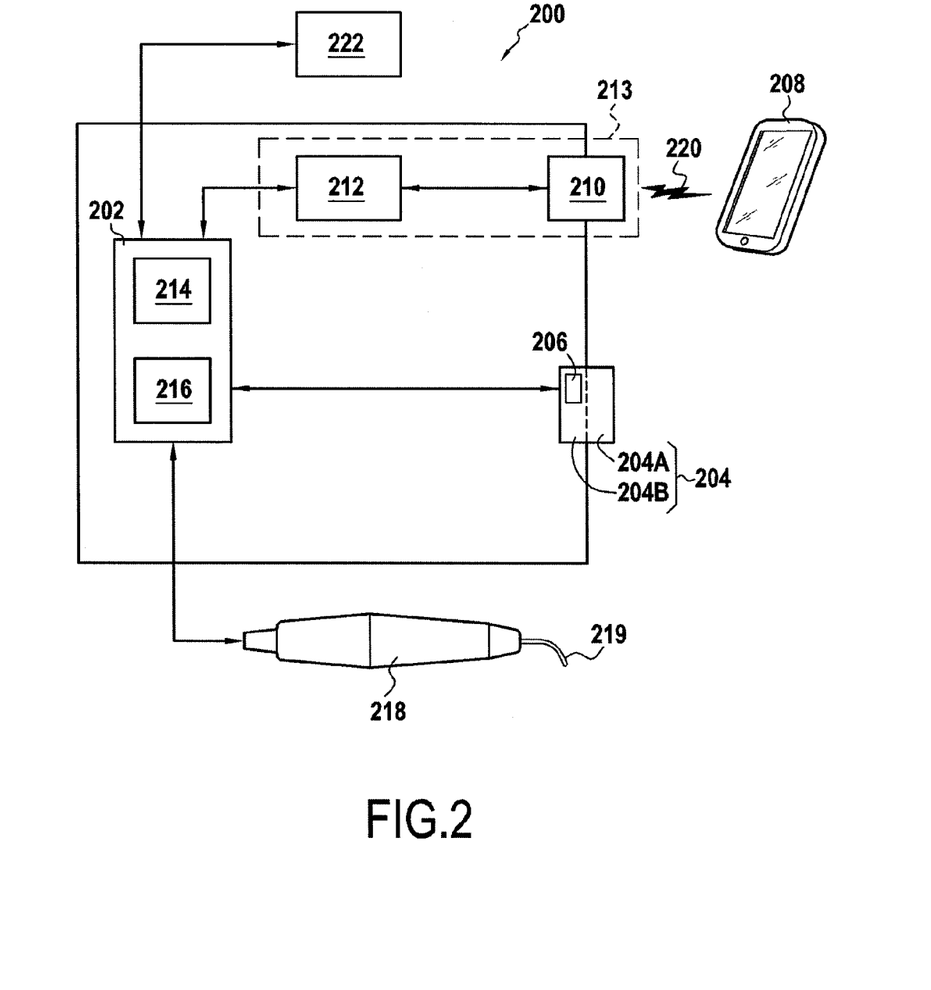
FIGS. 2, 3, and 4 are diagrammatic views of a control device for a surgical handpiece in a first embodiment of the invention.
Figure 3:
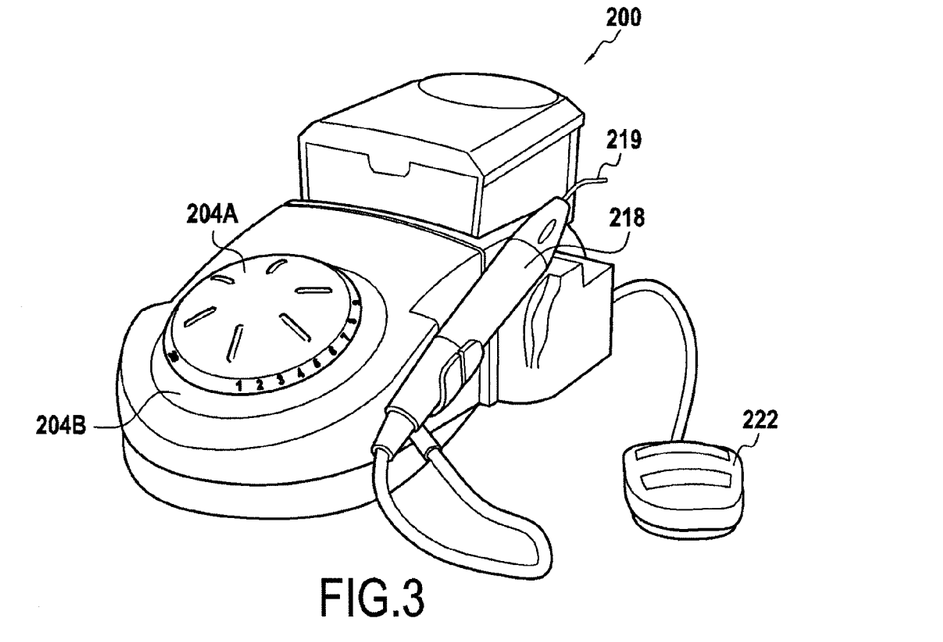
Figure 4:
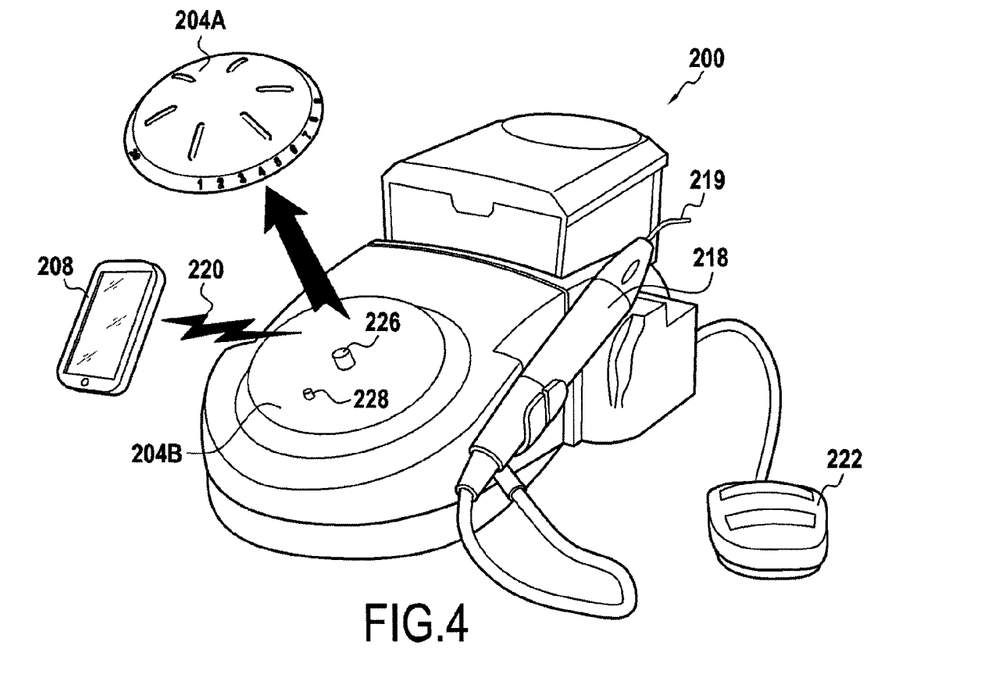

A first embodiment of the invention is described initially with reference to the control device 200 shown in FIGS. 2, 3, and 4.

The presently-described control device 200 serves to control a surgical handpiece 218 for dental care, e.g. for removing scale. This surgical handpiece 218 comprises in particular a mechanically constrained piezoelectric transducer (not shown) that is suitable for generating and transmitting ultrasound vibration to an insert 219 mounted at the distal end of the handpiece.

The control device 200 also comprises a control card 202 that corresponds in this example to a mother card including a processor and memories. The hardware architecture of this card is conventional and is therefore not described further in this document.

The mother card 202 governs the general operation of the control device 200 and in particular it includes a control module 214 in charge of adjusting the control parameters (or control settings) of the surgical handpiece 218. In the present embodiment, the control parameters controlled by the mother card 202 may comprise at least one parameter selected from: the electrical power delivered to the handpiece, and the fluid irrigation flow rate to the handpiece 218. By adjusting the irrigation flow rate in appropriate manner (running the pump quickly and continuously), it is possible in particular to drain the handpiece.

The control device 200 also comprises a daughter control card 212 coupled to the mother card. This daughter card 212 co-operates with the wireless communication interface 210 and enables a wireless communication link to be established between the interface 210 and entities external to the control device 200. In this example, consideration is given to the situation where a Bluetooth™ communication link is established between the wireless communication interface 210 and a remote terminal 208.

Nevertheless, it should be understood that wireless communication protocols other than Bluetooth™ can be envisaged in the context of the invention (such as the above-mentioned WiFi, Zigbee, and NFC protocols). The communication link 220 is preferably of the radio type, but other communication technologies are also possible, such as infrared.

The daughter card 212 is suitable for receiving and processing instructions for adjusting each control parameter of the handpiece 218, these instructions being issued from the remote terminal 208 via the wireless communication link 220, and then transmitted by the communication interface 210 to the daughter card 212. In this example, the daughter card 212 acts in particular to decode the wireless link.

The terminal 208 in this example constitutes remote control means in the meaning of the invention. The terminal 208 may be in the form of a communications module, e.g. of the mobile telephone or digital tablet type. A software application executed by the telephone enables an operator to control the control parameters of the handpiece 218 remotely.

Alternatively, the remote control means 208 may be in the form of any other type of wireless control, e.g. such as a conventional control pedal suitable for issuing adjustment instructions via a wireless communication link.

The daughter card 212 and the communication interface 210 also constitute wireless communication means 213 in the meaning of the invention suitable for communicating with the remote control means (i.e. the terminal 208 in this example) via the wireless communication link 220.

Thereafter the daughter card 212 transmits the instructions it receives to the mother card 202, after performing any necessary preprocessing, where appropriate.

In the presently-considered embodiment, it should be observed that the daughter card 212 is distinct from the mother card 202. Nevertheless, this configuration is not essential and merely constitutes one possible embodiment of the invention. Alternatively, the function of the daughter card 212 could be executed by the mother card 202 itself.

The control device 200 also includes local control means 204 present on the control device 200 itself. Using these local control means, the practitioner can adjust one or more of the control parameters of the handpiece 218.

In this first embodiment, the local control means 204 comprise a removable portion 204A and a stationary portion 204B of a Hall effect magnetic button. The stationary portion 204B is secured to the control device 200 and can co-operate with the removable portion 204A when it is mounted on the stationary portion 204B. In this example, the practitioner may remove the removable portion 204A manually and then put it back on the stationary portion 204B when it is desired to adjust the control parameters of the handpiece 218 directly on the housing of the control device 200.

As shown in FIG. 4, the stationary portion 204B in this example is fitted with a stud 226 configured to be engaged in a recess in the rear portion of the removable portion 204A while said removable portion 204A is in its working position on the control device 200. The operator can then adjust one or more control settings by turning the removable portion 204A, e.g. with the help of visual markers that may be arranged on the removable portion 204A (or possibly on the stationary portion 204B).

The stationary portion 204B also comprises an abutment 228 that makes it possible to prevent the removable portion 204A from turning when it reaches the end of its stroke (i.e. when the operator has reached a maximum possible adjustment value or a minimum possible adjustment value).

By detaching the removable portion 204A, the user can clean the front face of the control device 200 effectively, in particular concerning the stationary portion 204B, and can therefore maintain good hygiene for the control device 200, where this is often critical in the medical field.

Nevertheless, it should be understood that it is possible to have variants of this first embodiment in which the Hall effect magnetic button is replaced by any other type of button or local control means having a stationary portion 204B and a removable portion 204A. By way of example, the local control means 204 may correspond to an electrical button or to a button that operates with the help of optical means. By way of example, an optical type button may comprise a light-emitting diode (LED) mounted in the removable portion together with one or more photodetectors mounted facing it on the stationary portion so as to be capable of detecting the position of the LED, and thus the position of the removable portion 204A facing the stationary portion 204B.

More generally, the local control means 204 of the control device 200 are suitable for receiving instructions for adjusting one or more of the control parameters of the handpiece 218, these instructions being issued by the operator actuating the local control means 204 (e.g. turning the Hall effect magnetic button).

In this example, the control device 200 is also fitted with a control pedal 222 enabling the operator to switch the handpiece 218 on and off.

Furthermore, the mother card 202 comprises a selector module 216 suitable for selecting either the local control means 204, or the wireless communication means 213 for the purpose of adjusting the control setting(s). In this example the selector module 216 comprises selector means in the meaning of the invention.

The control module 214 is configured to adjust the control parameters of the surgical handpiece 218 as a function of the selection made by the selector module 216. In other words, the control module 214 takes account only of adjustment settings coming from the means selected by the selector module 216, namely: the wireless communication means 213 or, alternatively the local control means 204.

At any moment, only one of the wireless communication means 213 and the local control means 204 can be selected by the selector means 216 (i.e. it is not possible for both means 213 and 204 to be selected simultaneously).

In this first embodiment, the local control means 204 comprise detector means 206 for detecting the presence of the removable portion 204A on the control device 200. In other words, the detector means 206 are suitable for detecting the presence (and thus also, on the contrary, the absence) of the removable portion 204A on the stationary portion 204B.

By way of example, the detector means 206 may comprise optical means (e.g. a photodetector) making it possible to detect when the removable portion 204A is mounted in the working position on the stationary portion 204B of the local control means 204.

Still in this first embodiment, the selector means 216 are configured to select the local control means 204 automatically for the purpose of adjusting the control settings when the detector means 206 detect that the removable portion 204A is present on the stationary portion 204B. Under such circumstances, the control module 214 then takes account of adjustment instructions issued by the local control means 204 for adjusting the control parameters of the handpiece 218.

In contrast, when the detector means 206 detects that the removable portion 204A is absent (e.g. while the control device 200 is being cleaned), the selector means automatically select the wireless communication means 213 for adjusting the control parameters of the handpiece 218. Under such circumstances, the control module 214 takes account solely of adjustment instructions received by the wireless communication means 213 coming from the remote terminal 208 via the wireless communication link 220.

As mentioned above, when the removable portion 204A of the local control means 204 is present on the control device 200, only instructions coming from the button 204 are taken into account for adjusting the parameters. It should be observed that when the local control means 204 are selected by the selector means 216, the wireless communication link (of the Bluetooth™ type in this example) is not necessarily interrupted.

In a preferred variant, the wireless communication link 220 is maintained even when the presence of the removable portion 204A is detected by the detector means 206. This variant advantageously makes it possible to avoid undesirable waiting time resulting from the time taken for re-establishing the communication link 220 when the removable portion 204A is no longer present on the control device 200, where this waiting time might be of longer or shorter length. In this preferred variant, when the local control means are selected (because the removable portion 204A is present on the control device 200), the instructions received by the wireless communication means 213 are merely ignored by the mother card 202 (or possibly by the daughter card 212).

Figure 5:
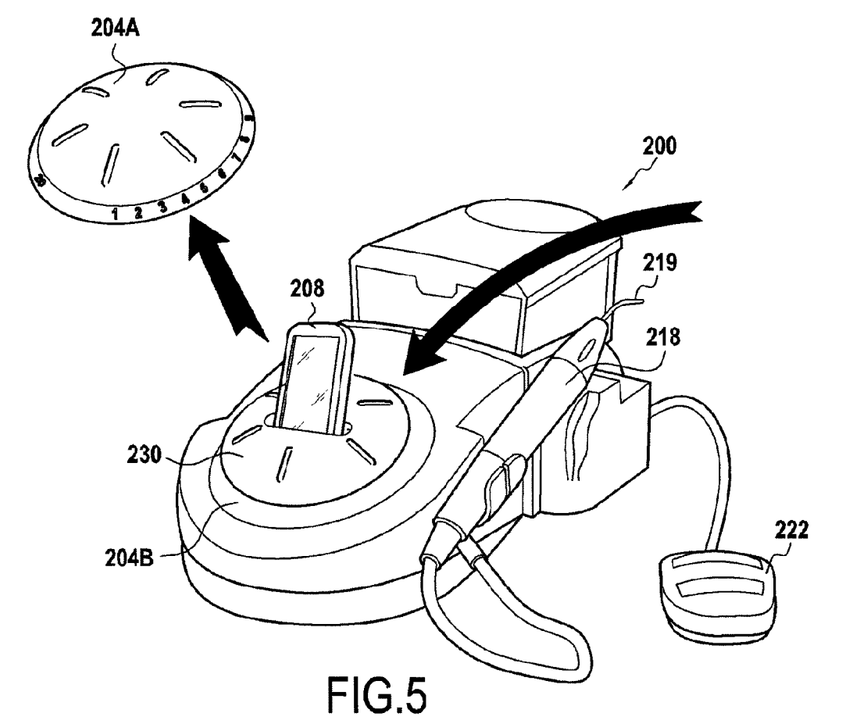
FIG. 5 is a diagrammatic view of a variant of the first embodiment shown in FIGS. 3 and 4.

In the variant shown in FIG. 5, the remote terminal 208 may be arranged on a stand 230 that can itself be put into position to take the place of the removable portion 204A.

Figure 6:
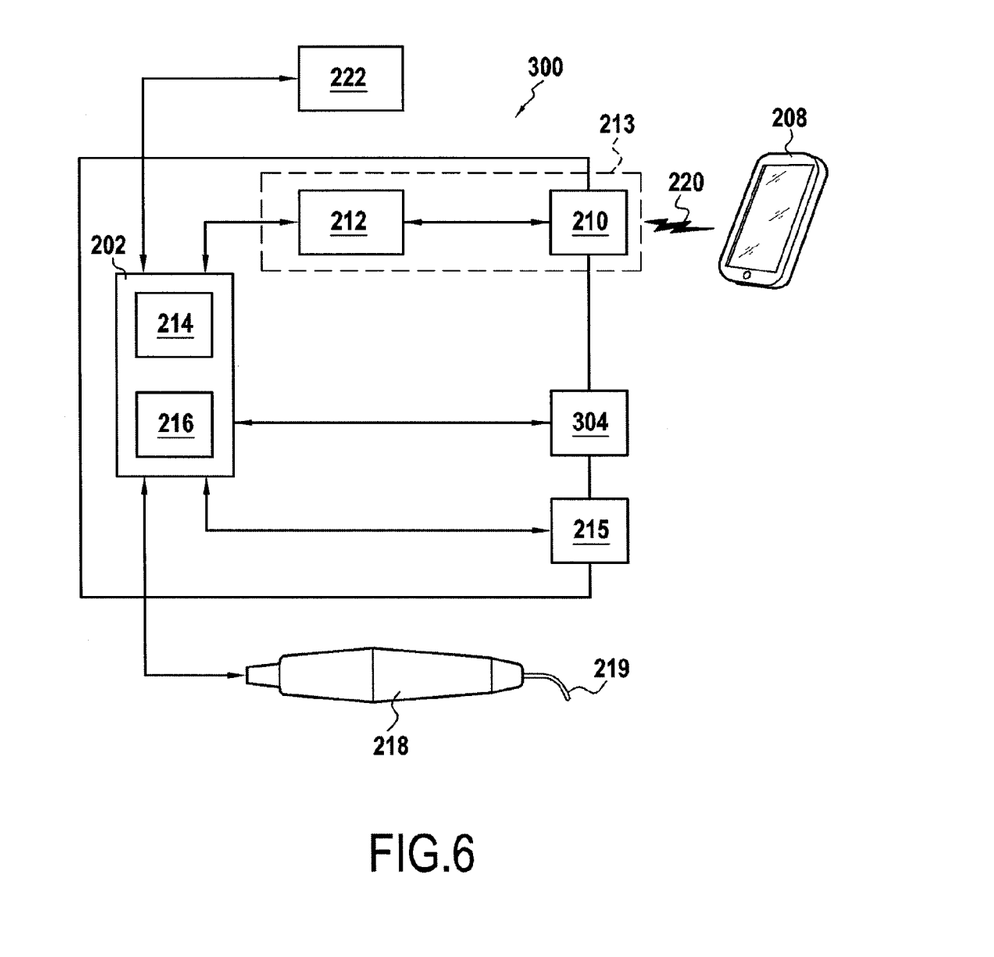
FIGS. 6 and 7 are diagrammatic views of a control device of a surgical handpiece in a second embodiment of the invention.
Figure 7:
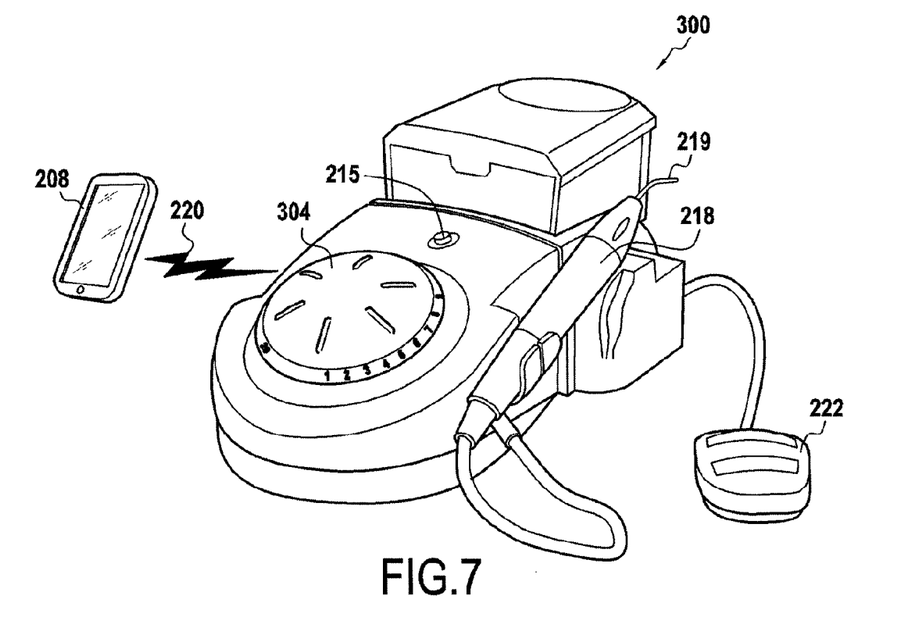

A control device 300 in a second embodiment of the invention is described below with reference to FIGS. 6 and 7.

This control device 300 comprises for the most part the same elements as those described above with reference to the control device 200. Elements that are common to both of the devices 200 and 300 thus have the same references and they are not described again.

The control device 300 differs from the above-described device 200 in that the local control means 304 do not have a removable portion. In this second embodiment, the local control means are in the form of a button 304 that can be turned relative to the housing of the control device 300 for the purpose of adjusting one or more control settings of the handpiece 218. Nevertheless, other forms of local control may be envisaged.

In this second embodiment, the local control means 304 therefore do not have any presence detector means 206 as described above for the first embodiment.

The control device 300 also has a switch 215 that, in this example, is in the form of a pushbutton arranged on the housing (nevertheless, other forms of switch could be envisaged by the person skilled in the art). The switch 215 can be activated manually by the operator and on being activated it serves to select either the local control means 304 or else the wireless communication means 213 for the purpose of adjusting each control parameter.

The invention makes it advantageously possible to make secure the adjustment of control settings of the surgical handpiece 208. By means of the invention, it is in particular still possible for the operator quickly to regain control over the handpiece 218 in the event of a failure occurring in the wireless communication 220 or in the event of any emergency situation (as explained above, emergency situations may have multiple origins).

The control device of the invention advantageously makes it possible to define priority levels between the local control means 204 and the remote control means 208: for example, in the event of a failure in receiving or processing adjustment instructions issued by the remote control means 208, it is still possible for the operator to regain control over the handpiece 218.

In the first embodiment (control device 200), as soon as the removable portion 204A is in its working position, the local control means 204 have priority over the remote control means 208, i.e. the local control means are selected by the selector means 216. Consequently, the instructions issued by the terminal 208 are ignored and only instructions coming from the button 204 are then taken into account for adjusting the handpiece 218.

In the second embodiment (control device 300), the operator can at any moment use the switch 215 to select either the local control means 304 or the remote communication means 213. Thus, in the event of a failure of the wireless communication link 220 or in the event of any other emergency situation, the operator can rapidly take control of the surgical handpiece 218 by selecting the button 304 to adjust control settings. In this way, the control device 200 is forced to ignore all instructions that might come from the remote control means via the wireless communication link 220.

The invention claimed is:

1. A control device for controlling a surgical handpiece, the device being suitable for controlling the surgical handpiece according to at least one control parameter, the control device comprising:
   local control means present on said control device;
   wireless communication means suitable for communicating with remote control means by a wireless communication link, the local control means and the wireless communication means being suitable for receiving instructions to adjust each control parameter;
   a control unit configured to simultaneously receive a signal from the local control means and a signal from the wireless communication means; and
   selector means for selecting either the local control means or the wireless communication means for adjusting each control parameter.

2. A control device according to claim 1, wherein the local control means include a removable portion;
   the control device also comprising detector means for detecting the presence of said removable portion on the control device;
   the selector means being configured to select the local control means automatically for adjusting each control parameter in the event of the presence of said removable portion being detected.

3. A control device according to claim 1, wherein the selector means comprise a manually-operable switch for selecting either the local control means or the wireless communication means for adjusting each control parameter.

4. A control device according to claim 1, wherein the wireless communication link is of the Bluetooth™ type.

5. A control device according to claim 1, wherein the local control means comprise a Hall effect magnetic button.

6. A control device according to claim 1, wherein the handpiece includes a piezoelectric transducer, said at least one parameter comprising at least one of the following: an electrical power level to be delivered to the handpiece; an irrigation flow rate for the handpiece; and activating or deactivating the handpiece.

7. An apparatus for controlling a surgical handpiece, the apparatus comprising:
   a control device according to claim 1;
   a handpiece having control parameters that are adjusted by said control device; and
   remote control means suitable for communicating with the wireless communication means of the control device via a wireless link.

8. A control appliance according to claim 7, wherein the remote control means are a communications module of the mobile telephone or digital tablet type.

9. A control device for controlling a surgical handpiece, the control device being suitable for controlling the surgical handpiece according to at least one control parameter, the control device comprising:
   a local controller present on said control device;
   a wireless communication device suitable for communicating with a remote controller by a wireless communication link, the local controller and the wireless communication device being suitable for receiving instructions to adjust each control parameter;
   a control unit configured to simultaneously receive a signal from the local controller and a signal from the wireless communication device; and
   a selector configured to select either the local controller or the wireless communication device for adjusting each control parameter.

10. A control device according to claim 9, wherein the local controller includes a removable portion;
   the control device also comprising a detector configured for detecting the presence of said removable portion on the control device;
   the selector being configured to select the local controller automatically for adjusting each control parameter in the event of the presence of said removable portion being detected.

11. A control device according to claim 9, wherein the selector comprises a manually-operable switch for selecting either the local controller or the wireless communication device for adjusting each control parameter.

12. A control device according to claim 9, wherein the wireless communication link is of the Bluetooth™ type.

13. A control device according to claim 9, wherein the local controller comprises a Hall effect magnetic button.

14. A control device according to claim 9, wherein the handpiece includes a piezoelectric transducer, said at least one parameter comprising at least one or more of the following:
   an electrical power level to be delivered to the handpiece;
   an irrigation flow rate for the handpiece; and
   activating or deactivating the handpiece.

15. An apparatus for controlling a surgical handpiece, the apparatus comprising:
   a control device according to claim 9;
   a handpiece having control parameters that are adjusted by said control device; and
   a remote controller suitable for communicating with the wireless communication device of the control device via a wireless link.

16. A control appliance according to claim 15, wherein the remote controller includes a communications module of the mobile telephone or digital tablet type.

* * * * *